(12) United States Patent
Kobilka et al.

(10) Patent No.: US 10,590,069 B2
(45) Date of Patent: Mar. 17, 2020

(54) PINENE-DERIVED DIISOCYANATES

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 22 days.

(21) Appl. No.: 15/727,439

(22) Filed: Oct. 6, 2017

(65) Prior Publication Data
US 2019/0106383 A1   Apr. 11, 2019

(51) Int. Cl.
| C07C 265/10 | (2006.01) |
| C07C 263/10 | (2006.01) |
| C08G 18/75 | (2006.01) |
| C07C 209/48 | (2006.01) |
| C07C 209/62 | (2006.01) |
| C07C 231/12 | (2006.01) |
| C07C 209/26 | (2006.01) |

(Continued)

(52) U.S. Cl.
CPC .......... *C07C 265/10* (2013.01); *C07C 209/26* (2013.01); *C07C 209/48* (2013.01); *C07C 209/62* (2013.01); *C07C 231/12* (2013.01); *C07C 253/10* (2013.01); *C07C 263/10* (2013.01); *C07C 265/14* (2013.01); *C08G 18/753* (2013.01); *C08G 18/755* (2013.01); *C08G 18/758* (2013.01); *C07C 2601/14* (2017.05); *C07C 2602/42* (2017.05)

(58) Field of Classification Search
CPC ........................... C07C 265/10; C07C 265/14
See application file for complete search history.

(56) References Cited

U.S. PATENT DOCUMENTS

| 5,506,301 A | * | 4/1996 | Marques | ............... | C07C 263/18 |
| | | | | | 524/284 |
| 7,381,766 B1 | | 6/2008 | Anderson | | |
| 9,757,492 B2 | | 9/2017 | Heckroth et al. | | |

(Continued)

OTHER PUBLICATIONS

Lesiak, Tadeusz. Abstract. Pro-Ecological syntheses of intermediates for the manufacture of polyurethanes. Part II. Addition of isocyanic acid to some alkenes and alkadienes. Polimery. vol. 40, Issue 02, pp. 83-88. 1995.*

Gotro, J., Guest post by Dr. Robert Humphreys, "The Winding Road to Renewable Thermoset Polymers Part 3: Thermoset Polyurethanes," Polymer Innovation Blog, Jul. 18, 2013, pp. 1-9. https://polymerinnovationblog.com/the-winding-road-to-renewable-thermoset-polymers-part-3-thermoset-polyurethanes/.

Quilter et al., "Polymerisation of a terpene-derived lactone: a bio-based alternative to ε-caprolactone†," Polymer Chemistry, Dec. 2016, 6 pages, Royal Society of Chemistry. DOI: 10.1039/c6py02033j.

(Continued)

*Primary Examiner* — Michael L Leonard
(74) *Attorney, Agent, or Firm* — Kelsey M. Skodje (57) ABSTRACT

A pinene-derived diisocyanate compound, a process for forming a pinene-derived diisocyanate compound, and an article of manufacture containing a polyurethane polymer are disclosed. The process for forming the pinene-derived diisocyanate compound includes oxidizing the pinene to form a pinene-derived ketone compound, converting the pinene-derived ketone compound to a diamine compound in subsequent reaction steps, and reacting the diamine compound with phosgene to form the pinene-derived diisocyanate compound. The polyurethane polymer is synthesized in a reaction between a pinene-derived diisocyanate compound and a polyol.

11 Claims, 6 Drawing Sheets

(51) Int. Cl.
C07C 253/10 (2006.01)
C07C 265/14 (2006.01)

(56) References Cited

U.S. PATENT DOCUMENTS

| | | | |
|---|---|---|---|
| 2007/0269365 A1* | 11/2007 | Weber | C01B 7/035 |
| | | | 423/502 |
| 2011/0124830 A1 | 5/2011 | Nakahara et al. | |
| 2011/0124918 A1 | 5/2011 | Ernst et al. | |
| 2011/0224395 A1* | 9/2011 | Carr | C07C 263/10 |
| | | | 528/44 |
| 2012/0142959 A1* | 6/2012 | Mattke | C01B 7/04 |
| | | | 560/347 |
| 2013/0130345 A1* | 5/2013 | Thai | C07C 1/247 |
| | | | 435/166 |
| 2015/0246873 A1 | 9/2015 | Laue et al. | |
| 2017/0044282 A1 | 2/2017 | Howdle et al. | |

OTHER PUBLICATIONS

"Market Study: Ployurethanes (PUR) and Isocyanates (MDI & TDI)," [2nd Edition], 2016, Printed: May 25, 2017, pp. 1-3, http://www.ceresana.com/en/market-studies/plastics/pur-isocyanates/.
"Pinene Isomerisation—Alpha to Beta," SciFinder Results, pp. 1-52, © 2017.
"Pinene Isomerisation—Beta to Alpha," SciFinder Results, pp. 1-5, © 2017.
"Pinene Isocyanate Synthetics," SciFinder Results, pp. 1-5.

* cited by examiner

PINENE-DERIVED DIISOCYANATES

BACKGROUND

The present disclosure relates to bio-renewable compounds and more specifically to diisocyanates synthesized from pinene.

Bio-based, sustainable compounds can be used in applications and syntheses of compounds that previously required petroleum-based raw materials. For example, bio-based compounds can be building blocks for plastics, adhesives, pharmaceuticals, etc. There are numerous strategies for efficiently and inexpensively producing bio-based polymers on an industrial scale. Examples of these strategies can be found in fermentation technologies, membrane technologies, and genetic engineering. Alpha-pinene (2,6,6-trimethylbicyclo[3.1.1]hept-2-ene) and beta-pinene ((1S, 5S)-6,6-dimethyl-2-methylenebicyclo[3.1.1]heptane) are examples of bio-based compounds. Alpha- and beta-pinene are obtained from sources that can include pine resin, turpentine, sage, etc.

SUMMARY

Various embodiments of the present disclosure are directed to a pinene-deriveddiisocyanate compound. The pinene-derived diisocyanate compound can be derived from alpha- or beta-pinene isolated from one or more sources such as conifer resin, turpentine, *Heterotheca, Artemisia tridentata, Sideritis, Salvia, Cannabis, Pistacia terebinthus, Cuminum cyminum, Humulus lupulus, Pinus pinaster*, and *Clausena anisata*.

Additional embodiments are directed to a process of forming an alpha- or beta-pinene-derived diisocyanate compound, which can include obtaining pinene, oxidizing the pinene to form a pinene-derived ketone compound, converting the pinene-derived ketone compound to a diamine compound in subsequent reaction steps, and reacting the diamine compound with phosgene to form the pinene-derived diisocyanate compound. The process can also include reacting the pinene-derived ketone compound with potassium cyanide. Further, the process can include reacting the pinene-derived diisocyanate compound with a polyol in a polymerization reaction that forms a polyurethane polymer. Additionally, the process can include adding at least one additive, such as a cross-linker, a chain-extender, a blowing agent, an inorganic pigment, an organic pigment, a flame retardant, a surfactant, a filler, a smoke suppressant, and a plasticizer to the polymerization reaction.

Further embodiments are directed to an article of manufacture that includes a polyurethane polymer, wherein the polyurethane polymer is formed in a polymerization reaction between a pinene-derived diisocyanate compound and a polyol. Further, the polyurethane polymer can be a component of an integrated circuit package.

DETAILED DESCRIPTION

Polyurethanes are polymers containing organic monomers connected by urethane linkers. Polyurethanes are most commonly formed by reacting di- or polyisocyanates with polyols (i.e., organic compounds with more than one hydroxyl group). The properties and applications of a polyurethane are determined by the degree of cross-linking, structure of di- or polyisocyanate and polyol monomers, relative lengths of segments of its chains, presence of additives, etc. Polyurethanes can be thermosetting polymers (i.e., polymers that strengthen when heated), or thermoplastic polymers (i.e., polymers that soften when heated), depending on the polymer structure. The properties of polyurethanes are discussed in greater detail below.

Polyurethanes are used in a wide variety of applications. Examples of these applications can include coatings (e.g., UV resistant coatings), foams (e.g., acoustic foams, insulating foams, etc.), paints, hard plastics, flexible plastics, wheels, enclosures for electronic parts, varnishes, adhesives, solid rocket fuel, textiles, sporting equipment, footwear, sealants, air-retentive bladders, packaging, synthetic leather, etc. Polyurethanes have traditionally been made from substances that require petroleum-based, non-renewable raw materials. However, due to the rising costs of fossil fuels, and increasing environmental regulatory controls, there is a growing interest in obtaining materials from renewable sources.

Bio-based compounds are compounds that are isolated or derived from renewable, biological sources, such as plants, fungi, microorganisms, animal products, and atmospheric gases. Bio-based compounds are increasingly being used in the syntheses of substances that previously required petroleum-based raw materials. Bio-based compounds have applications in sustainable, or "green," materials because they are obtained from renewable sources. Bio-based polymers are polymers that are synthesized, at least in part, from bio-based starting materials. In some examples, bio-based polymers and petroleum-based polymers are blended to form a polymer composite. However, polymers can also be entirely bio-based, or produced from a combination of bio- and petroleum-based monomers.

Advances in biotechnology have provided numerous strategies for efficiently and inexpensively producing bio-based compounds on an industrial scale. Examples of these strategies can be found in fermentation technologies, membrane technologies, and genetic engineering. Biotechnological strategies can include plant-based and microorganism-based approaches. Plant-based approaches involve obtaining a material directly from a plant, or growing plant tissues or cells that produce bio-based compounds from various substrates using their own biosynthetic pathways. Microorganism-based approaches involve using native or genetically modified fungi, yeast, or bacteria to produce a desired compound from a structurally similar substrate.

Pinene is one example of a bio-based compound that can have industrial applications. Pinene can be obtained from conifer (e.g., pine) resin, as well as numerous other plants. Examples of plants that contain pinene can include *Heterotheca, Artemisia tridentata, Sideritis, Salvia, Cannabis, Pistacia terebinthus, Cuminum cyminum, Humulus lupulus, Pinus pinaster, Clausena anisata*, etc. There are two isomers of pinene, alpha (α)-pinene (2,6,6-trimethylbicyclo[3.1.1] hept-2-ene) and beta (β)-pinene ((1S, 5S)-6,6-dimethyl-2-methylenebicyclo[3.1.1]heptane). These two isomers can be converted into one another via isomerization reactions.

According to the present disclosure, diisocyanate compounds are derived from pinene. These diisocyanate compounds can be used in the production of polyurethanes. The selection of a diisocyanate for this purpose affects the properties of the resulting polyurethane (e.g., softness, elasticity, rigidity, UV resistance, etc.). Therefore, the ability to synthesize a wide variety of possible structures for bio-based diisocyanates will allow bio-based polyurethanes to replace a wide variety of petroleum-based polyurethanes. Pinene provides an avenue for the synthesis of various types of diisocyanates. Additionally, it should be noted that, while diisocyanates are most commonly polymerized to form polyurethanes, these compounds can have other applications. For example, diisocyanates can be used as adhesives or in biomedical applications.

Figure 1:
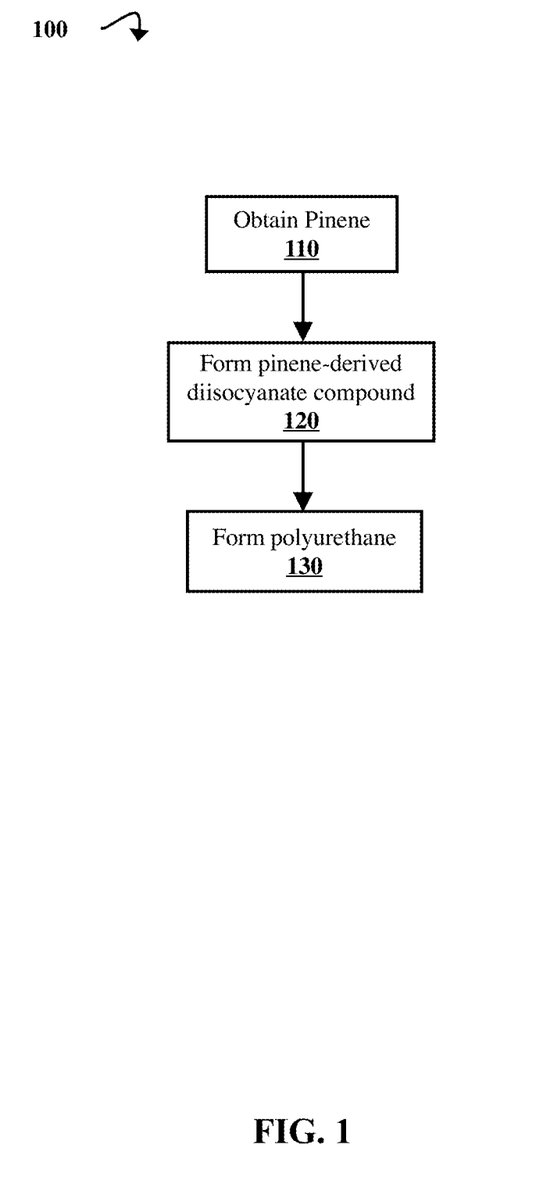
FIG. 1 is a flow diagram illustrating a process of forming a pinene-derived polyurethane polymer.

FIG. 1 is a flow diagram illustrating a process 100 of forming a polyurethane polymer by polymerizing a pinene-derived diisocyanate. Process 100 begins with the obtainment of pinene. This is illustrated at step 110. Pinene is isolated from a material, such as a resin or turpentine, obtained from a plant source. Plant sources of pinene are discussed in greater detail above. Pinene is isolated as alpha-pinene, beta-pinene, or a combination of the two. Further, alpha- and beta-pinene can be converted into one another via isomerization reactions. The isomer of pinene that is selected determines the identities of diisocyanates that can be produced in subsequent syntheses. Isomerization reactions between alpha- and beta-pinene are discussed in greater detail with respect to FIG. 2.

Process 100 continues with the formation of a pinene-derived diisocyanate compound. This is illustrated at step 120. The diisocyanate synthesis begins with either alpha- or beta-pinene. The selected pinene isomer is then reacted in an oxidation reaction to form a ketone moiety. Subsequent reactions produce a diamine compound, which is reacted with phosgene ($COCl_2$) to form the diisocyanate. A diisocyanate is a compound having two isocyanate functional groups. An isocyanate functional group has the formula —NCO, where a nitrogen atom (N) and an oxygen atom (O) are each bound to the same carbon atom (C) by double bonds. The N atom of each isocyanate functional group is bound to a different carbon atom in the diisocyanate compound. The syntheses and structures of pinene-derived diisocyanate compounds are discussed in greater detail with respect to FIGS. 3A-3C.

The pinene-derived diisocyanate compound is polymerized to form a polyurethane polymer. This is illustrated at step 130. This polymerization involves a reaction between the pinene-derived diisocyanate compound and a polyol. The properties of the resulting polyurethane can be controlled by multiple factors. For example, if a polyol that will contribute long, flexible segments is used in the reaction, the resulting polyurethane will be soft and elastic. A polyurethane with high elasticity is also formed when long segments are combined with low degrees of cross-linking. If short segments are combined with high degrees of cross-linking, the polyurethane will be hard. Further, polyurethane foams are made from polymers with long chains and intermediate degrees of cross-linking. The polymerization of the pinene-derived diisocyanate compounds is discussed in greater detail with respect to FIG. 4.

Figure 2:
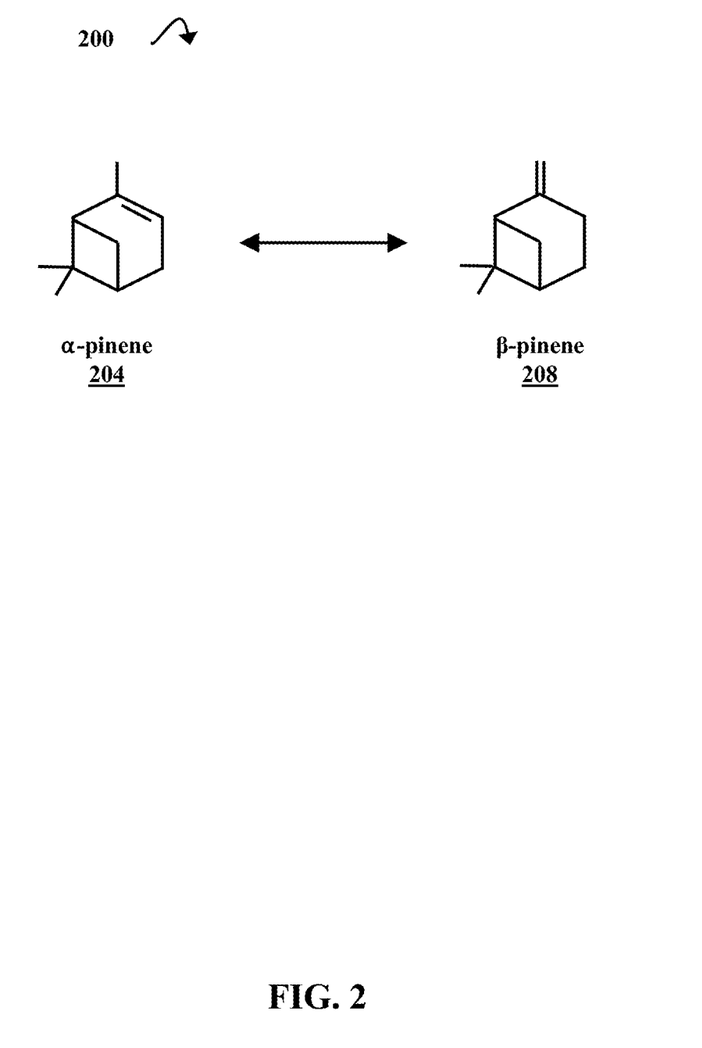
FIG. 2 is a chemical reaction diagram illustrating the isomerization of pinene, according to some embodiments of the present disclosure.

FIG. 2 is a chemical reaction diagram 200 illustrating the isomerization of pinene, according to some embodiments of the present disclosure. There are a variety of reactions that can result in pinene isomerization. In one example, alpha (α)-pinene 204 is converted to beta (β)-pinene 208 in a reaction with hydrogen peroxide ($H_2O_2$), catalyzed by sodium tungstate ($Na_2WO_4$) in a water/trichloromethane ($H_2O/CHCl_3$) solution. In another example, alpha-pinene 204 is isomerized in a reaction with hydrochloric acid (HCl) in $H_2O$. This reaction is carried out at approximately 120° C., and catalyzed by palladium(II) chloride ($PdCl_2$). In an example of beta-pinene 208 isomerization, beta-pinene 208 is converted to alpha-pinene 204 in a reaction with hydrogen ($H_2$) in benzene. Additionally, beta-pinene 208 can be converted to alpha-pinene 204 in a reaction with potassium hydride (KH) in 1,3-diaminopropane ($H_2N(CH_2)_3NH_2$) under an inert atmosphere.

Figure 3A:
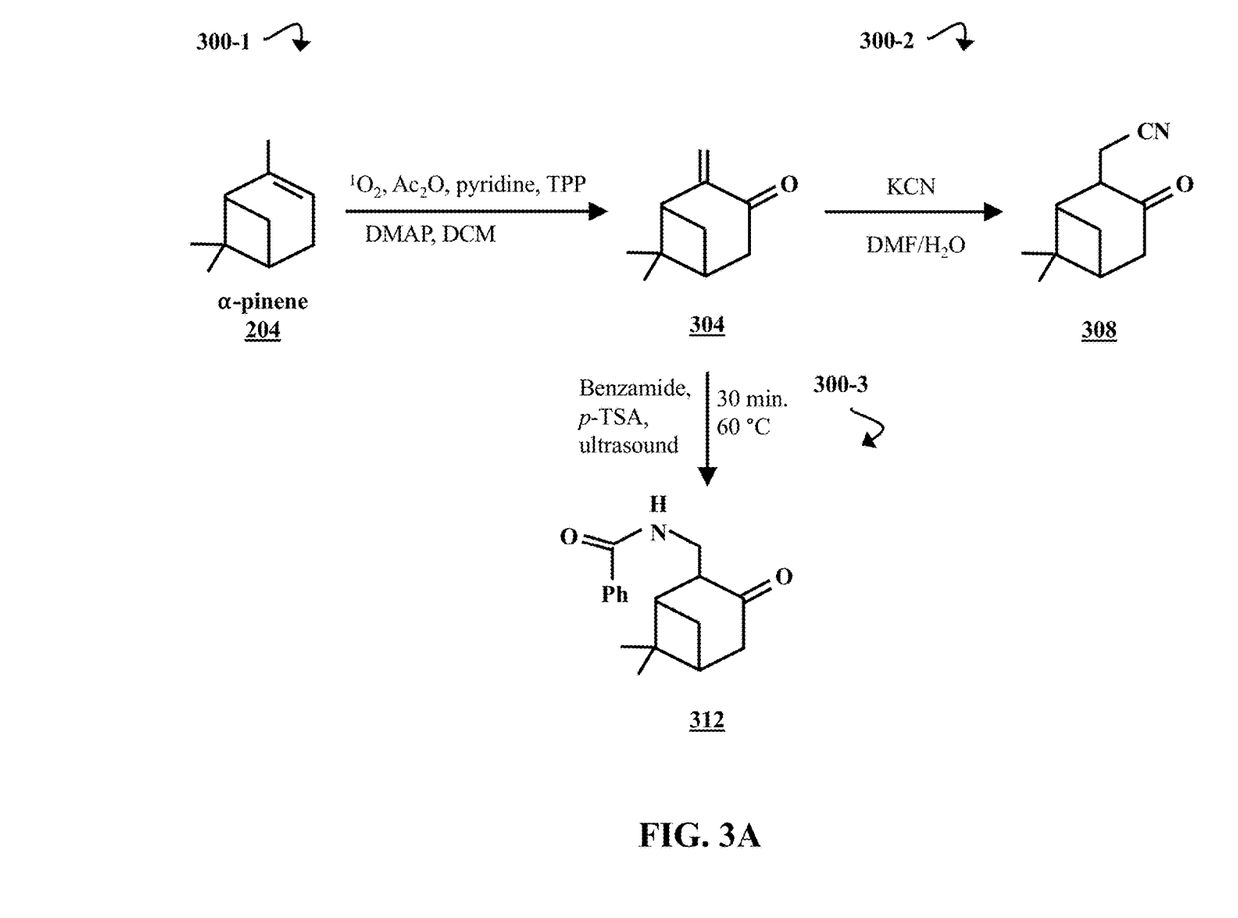
FIG. 3A is a chemical reaction diagram illustrating processes of synthesizing alpha-pinene derivatives, according to some embodiments of the present disclosure.

FIG. 3A is a chemical reaction diagram illustrating processes 300-1, 300-2, and 300-3 of forming derivatives 304, 308, and 312 of alpha-pinene 204, according to some embodiments of the present disclosure. In process 300-1, alpha-pinene 204 is oxidized to form an alpha-pinene-derived ketone compound 304 by a catalyzed oxidation reaction. In this oxidation reaction, acetic anhydride ($Ac_2O$) and pyridine are added to a mixture of tetraphenylporphyrin (TPP), dimethylaminopyridine (cat. DMAP), and alpha-pinene 204 in dichloromethane (DCM). The mixture is stirred at room temperature (i.e., ~20° C.-27° C.) for approximately eighteen hours under singlet oxygen ($^1O_2$), which is generated by mixing with an organic dye (e.g., rose bengal, methylene blue, porphyrins, etc.), and applying radiation from at least one 20 W white light (i.e., light that includes wavelengths of approximately 390 nm-700 nm) to the reaction mixture. However, $^1O_2$ can be generated by other methods. Examples of these methods can include decomposition of triethylsilyl hydrotrioxide, an aqueous reaction of hydrogen peroxide with sodium hypochlorite, decomposition of phosphite ozonides, etc.

In process 300-2, the alpha-pinene-derived ketone compound 304 is reacted with potassium cyanide (KCN) in a dimethylformamide/water ($DMF/H_2O$) solution, producing an alpha-pinene-derived nitrile compound 308. In process 300-3, ultrasound is applied to a mixture of the alpha-pinene-derived ketone compound 304, benzamide, and p-toluene sulfonic acid (p-TSA). The mixture is reacted for approximately thirty minutes at about 60° C., and produces an alpha-pinene-derived carboxamide compound 312. It should be noted that, in some embodiments, benzamide is replaced by other organic amides (e.g., acetamide, propionamide, butyramide, pentanamide, etc.).

Figure 3B:
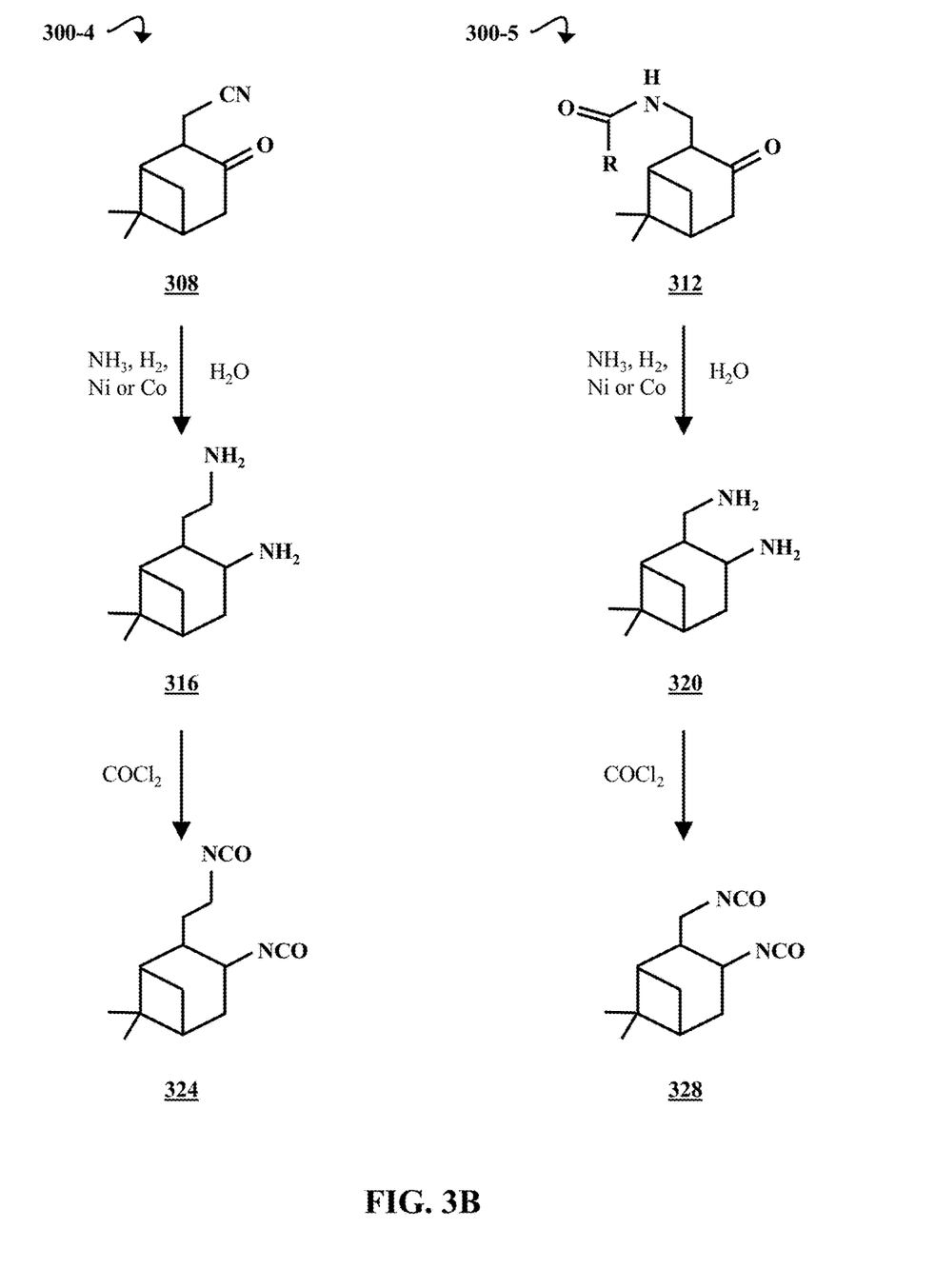
FIG. 3B is a chemical reaction diagram illustrating processes of synthesizing alpha-pinene-derived diisocyanates, according to some embodiments of the present disclosure.

FIG. 3B is a chemical reaction diagram illustrating processes 300-4 and 300-5 of forming alpha-pinene-derived diisocyanate compounds 320 and 328, according to some embodiments of the present disclosure. In the first step of both processes 300-4 and 300-5, the alpha-pinene-derived compounds 308 and 312 are converted into diamines by a reductive amination. In the reductive amination, the selected alpha-pinene compound 308 or 312 is reacted in an aqueous solution ($H_2O$) with gaseous ammonia ($NH_3$) and hydrogen ($H_2$). The reaction is catalyzed by a nickel (Ni) or cobalt (Co) catalyst. The reductive amination of the alpha-pinene-derived nitrile compound 308 and the alpha-pinene-derived carboxamide compound 312 produce alpha-pinene-derived diamine compounds 316 and 320, respectively.

In the second step of both processes 300-4 and 300-5, the alpha-pinene-derived diamine compounds 316 and 320 are each reacted with phosgene ($COCl_2$). The phosgene reaction converts the amine functional groups on compounds 316 and 320 to isocyanate functional groups. The reaction with alpha-pinene-derived diamine compound 316 in process 300-4 produces a first alpha-pinene-derived diisocyanate compound 324. The reaction with alpha-pinene-derived diamine compound 320 in process 300-5 produces a second alpha-pinene-derived diisocyanate compound 328.

Figure 3C:
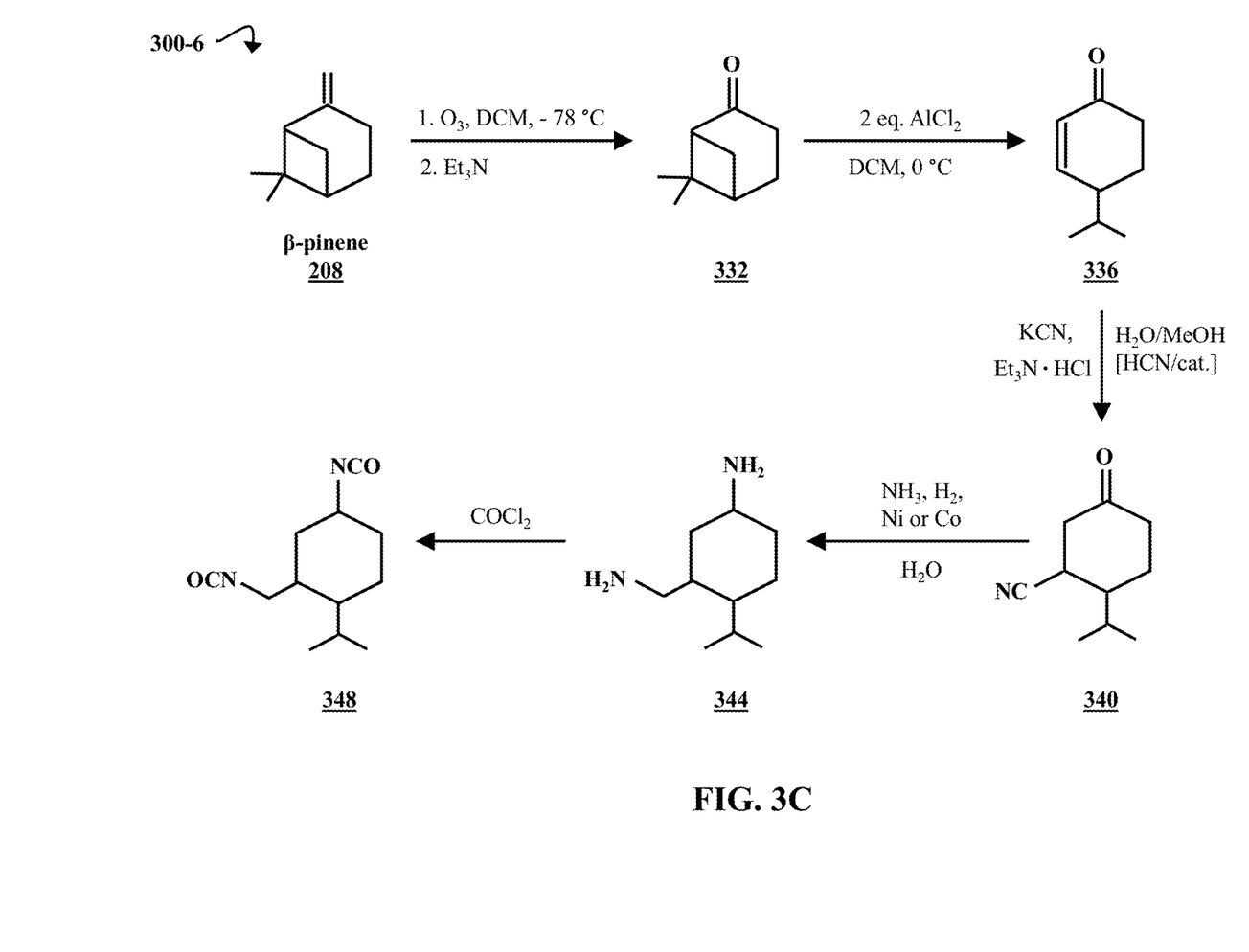
FIG. 3C is a chemical reaction diagram illustrating a process of synthesizing a beta-pinene-derived diisocyanate, according to some embodiments of the present disclosure.

FIG. 3C is a chemical reaction diagram illustrating a process 300-6 of forming a beta-pinene-derived diisocyanate compound 348, according to some embodiments of the present disclosure. In the first step of process 300-6, beta-pinene 208 is oxidized in an ozonolysis reaction. In this reaction, beta-pinene 208 is reacted with ozone ($O_3$) at approximately −78° C. in dichloromethane (DCM). Triethylamine ($Et_3N$) is added to the reaction mixture, and the exocyclic double bond on beta-pinene 208 is converted to a ketone moiety, forming nopinone 332. In the second step of process 300-6, nopinone 332 is reacted with approximately two equivalents of aluminum chloride ($AlCl_3$) in DCM at approximately 0° C. This Lewis acid-promoted isomerization reaction produces cryptone 336.

A nitrile moiety is added to cryptone 336 in the third step of process 300-6. In this step, potassium cyanide (KCN) and triethylamine hydrochloride ($Et_3N.HCl$) are combined with cryptone 336 in a water/methanol solution ($H_2O/MeOH$). This hydrogen cyanide (HCN) catalyzed reaction produces a beta-pinene-derived nitrile compound 340. The nitrile compound 340 is reacted in a reductive amination under conditions that are substantially similar to the first steps in processes 300-4 and 300-5. The nitrile compound 340 is reacted in an aqueous solution ($H_2O$) with gaseous ammonia ($NH_3$) and hydrogen ($H_2$). This reaction is catalyzed by a nickel (Ni) or cobalt (Co) catalyst, and produces a beta-pinene-derived diamine compound 344. The diamine compound 344 is then reacted with phosgene ($COCl_2$) to form the beta-pinene-derived diisocyanate compound 348.

Figure 4:
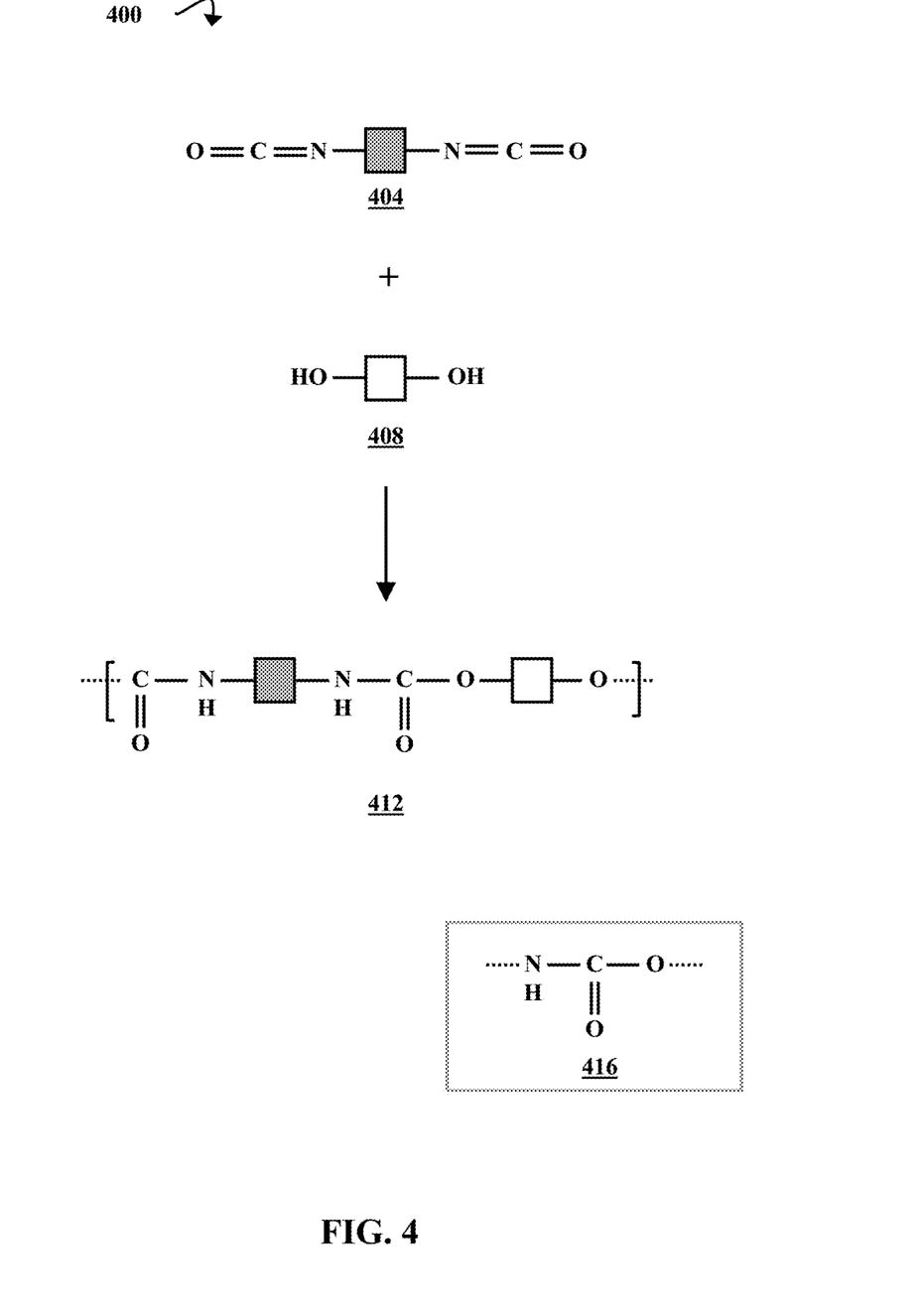
FIG. 4 is a chemical reaction diagram illustrating the polymerization of a generic diisocyanate, according to some embodiments of the present disclosure.

FIG. 4 is a chemical reaction diagram illustrating a process 400 of polymerizing a generic pinene-derived diisocyanate compound 404, according to some embodiments of the present disclosure. The polymerization process 400 produces a polyurethane polymer 412, and can be carried out with a variety of polymerization conditions. The generic pinene-derived diisocyanate compound 404 represents pinene-derived diisocyanate compounds 324, 328, or 348. The pinene-derivative cores of the pinene-derived diisocyanate derivatives 324, 328, or 348 (i.e., the parts of the diisocyanate molecule other than the isocyanate functional groups) are represented by a gray box in the generic pinene-derived diisocyanate 404. The isocyanate functional groups are illustrated as being attached to the gray box in the generic pinene-derived diisocyanate compound 404 for simplicity.

In process 400, the diisocyanate compound 404 is reacted with a compound having at least two hydroxyl groups (i.e., a polyol). For simplicity, this polyol is illustrated as a generic polyol 408 represented by a white box with two hydroxyl groups attached. However, polyols with more than two hydroxyl groups can be used as well. Further, in some embodiments, the polyols 408 can have additional functional groups, such as esters, ethers, amides, acrylates, metals, metalloids, etc. Examples of polyols 408 that will react with the diisocyanate compounds of the present disclosure to form a polyurethane can include polyether polyols, polyester polyols, polycarbonate polyols, graft polyols, polycaprolactone polyols, polybutadiene polyols, polysulfide polyols, polyols derived from vegetable oils, etc. The size and structure of the polyol affect the properties of the resulting polyurethane. For example, a greater number of functional groups can provide a higher degree of cross-linking, and a larger polyol 408 can lead to a polyurethane 408 with longer chains. The effects of chain length and cross-linking on the properties of the resulting polyurethane are discussed in greater detail with respect to FIG. 1.

The generic diisocyanate 404 and generic polyol 408 react to form a generic polyurethane 412. In the polymerization reaction, the hydroxyl groups and isocyanate groups react with one another to form the polyurethane's characteristic urethane links 416. The polymerization reaction 400 can be promoted under various reaction conditions. For example, a tertiary amine (e.g., 1,4-diazabicyclo[2.2.2]octane, bis-(2-dimethylaminoethyl)ether, N,N-dimethylaminopropylamine, N,N-dimethylcyclohexylamine, N,N,N',N',N"-pentamethyldiethylene-triamine, triethylenediamine, diethanolamine, 2(2-dimethylamino-ethoxy)ethanol, N-[2-(dimethylamino)ethyl]-N-methylethanolamine, dimethylethanolamine, 3-dimethylamino-N,N-dimethyl-propionamide, N-ethylmorpholine, etc.) can catalyze the reaction. Further, in some embodiments the polymerization is catalyzed by metal based catalysts (e.g., bismuth based catalysts, tin based catalysts, zinc based catalysts, potassium based catalysts, etc.). Additional examples of catalysts that can be used can include alkali metal salts of carboxylic acids and phenols. The polymerization is aided by ultraviolet (UV) light in some embodiments.

Cross-linkers and chain-extenders can also be added to the polymerization reaction mixture. Examples of compounds that can be used as cross-linkers or chain-extenders can include ethylene glycol, di- or triethylene glycol, propylene glycol, di- or tripropylene glycol, 1,3-propanediol, 1,3- or 1,4-butanediol, neopenyl glycol, 1,6-hexanediol, 1,4-cyclohexanedimethanol, hydroquinone bis(2-hydroxyethyl) ether, ethanolamine, di- or triethanolamine, methyldiethanolamine, phenyldiethanolamine, glycerol, trimethylolpropane, 1,2,6-hexanetriol, pentaerythritol, N,N,N',N'-tetrakis-(2-hydroxypropyl)ethylenediamine; diethyltoluenediamine, dimethyl-thio-toluenediamine, etc.

Properties of the polyurethane 412 can be affected by a variety of other additives as well. For example, if a blowing agent (e.g., carbon dioxide ($CO_2$), pentane, hydrazine, 1,1,1,2-tetrafluoroethane, 1,1,1,3,3-pentafluoropropane, etc.) is added or formed during the polymerization, a polyurethane foam will be produced. Additional examples of additives can include inorganic pigments (e.g., titanium dioxide, iron oxide yellow, nickel titanates, chrome titanates, chrome yellow, cadmium yellow, iron oxide brown, iron oxide red, cadmium red, iron/manganese mixed metal oxide black, iron oxide black, carbon black, mixed metal oxide blue, chrome oxide green, etc.), organic pigments (e.g., phthalocyanine blue, phthalocyanine green, perylene red, quinacridone red, monoazo yellow, isoindoline yellow, monoaryide yellow, etc.), flame retardants (e.g., phosphorus-based organic compounds, halogen-containing compounds, phosphorus-based inorganic compounds, etc.), surfactants (e.g., polydimethylsiloxane-polyoxyalkylene block copolymers, silicone oils, nonylphenol ethoxylates, etc.), fillers (e.g., plaster, glass microspheres, talc, marble dust, sand, ground limestone, bronze powder, fibers, etc.), smoke suppressants (e.g., trialkyl phosphate, ferrocene, tin compounds, etc.), plasticizers (e.g., diisooctyl phthalate, organophosphates, glycols/ polyethers, polymeric plasticizers, adipates, sebacates, maleates, trimellitates, di- or tricarboxylic ester-based plasticizers, etc.), etc.

One example of an application of polyurethanes formed, at least in part, from pinene-derived diisocyanates is in plastics used in electronics hardware, such as integrated circuit packages. Additional applications can include acoustic dampening, cushioning, plastics, synthetic fibers, insulation, coatings, etc. The polyurethanes can also be used to make adhesives such as bio-adhesives, elastomers, thermoplastics, emulsions, thermosets, etc. Further, materials containing the flame retardant itaconic acid-based compounds can be incorporated into various devices with electronic components that can include printed circuit boards (PCBs), semiconductors, transistors, optoelectronics, capacitors, resistors, chip carriers, etc. Additional examples of polyurethane applications are discussed in greater detail above.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of pinene-based diisocyanates and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A process of forming a pinene-derived diisocyanate compound, comprising:
   obtaining pinene;
   oxidizing the pinene to form a pinene-derived ketone compound;
   converting the pinene-derived ketone compound to a diamine compound in subsequent reaction steps; and
   reacting the diamine compound with phosgene to form the pinene-derived diisocyanate compound.

2. The process of claim 1, wherein one of the subsequent reaction steps is a reaction between the pinene-derived ketone compound and potassium cyanide.

3. The process of claim 1, wherein the pinene is alpha-pinene.

4. The process of claim 1, wherein the pinene is beta-pinene.

5. The process of claim 1, further comprising isomerizing the pinene.

6. The process of claim 1, wherein the pinene-derived diisocyanate compound has a formula of:

7. The process of claim 1, wherein the pinene-derived diisocyanate compound has a formula of:

8. The process of claim 1, wherein the pinene-derived diisocyanate compound has a formula of:

9. The process of claim 1, further comprising reacting the pinene-derived diisocyanate compound with a polyol in a polymerization reaction.

10. The process of claim 9, wherein the polymerization reaction forms a polyurethane polymer.

11. The process of claim 9, further comprising adding at least one additive selected from a group consisting of a cross-linker, a chain-extender, a blowing agent, an inorganic pigment, an organic pigment, a flame retardant, a surfactant, a filler, a smoke suppressant, and a plasticizer to the polymerization reaction.

* * * * *